(12) United States Patent
Baum et al.

(10) Patent No.: US 6,589,329 B1
(45) Date of Patent: Jul. 8, 2003

(54) COMPOSITION AND PROCESS FOR PRODUCTION OF COPPER CIRCUITRY IN MICROELECTRONIC DEVICE STRUCTURES

(75) Inventors: Thomas H. Baum, New Fairfield, CT (US); Chongying Xu, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/522,102

(22) Filed: Mar. 9, 2000

(51) Int. Cl.$^7$ .......................... C23C 16/16; C23C 16/08
(52) U.S. Cl. ......................... 106/287.15; 106/287.18; 427/253; 427/99; 556/112
(58) Field of Search ........................ 106/287.18, 287.15; 427/99, 252, 253; 556/112

(56) References Cited

U.S. PATENT DOCUMENTS

| | | | |
|---|---|---|---|
| 3,356,527 A | | 12/1967 | Moshier et al. |
| 3,594,216 A | | 7/1971 | Charles et al. |
| 5,085,731 A | | 2/1992 | Norman et al. |
| 5,094,701 A | | 3/1992 | Norman et al. |
| 5,096,737 A | * | 3/1992 | Baum et al. ............... 427/123 |
| 5,098,516 A | | 3/1992 | Norman et al. |
| 5,144,049 A | | 9/1992 | Norman et al. |
| 5,187,300 A | | 2/1993 | Norman |
| 5,204,314 A | | 4/1993 | Kirlin et al. |
| 5,220,044 A | | 6/1993 | Baum |
| 5,225,561 A | | 7/1993 | Kirlin et al. |
| 5,280,012 A | | 1/1994 | Kirlin et al. |
| 5,280,664 A | | 1/1994 | Gardiner et al. |
| 5,322,712 A | | 6/1994 | Norman et al. |
| 5,358,743 A | | 10/1994 | Hampden-Smith et al. |
| 5,362,328 A | | 11/1994 | Gardiner et al. |
| 5,453,494 A | | 9/1995 | Kirlin et al. |
| 5,536,323 A | | 7/1996 | Kirlin et al. |
| 5,711,816 A | | 1/1998 | Kirlin et al. |
| 5,744,192 A | | 4/1998 | Nguyen et al. |
| 5,820,664 A | | 10/1998 | Gardiner et al. |
| 5,919,522 A | | 7/1999 | Baum et al. |
| 5,994,571 A | | 11/1999 | Zhuang et al. |
| 6,337,148 B1 | * | 1/2002 | Xu et al. ............... 428/675 |

FOREIGN PATENT DOCUMENTS

EP 0852229 7/1998

OTHER PUBLICATIONS

U.S. patent application Ser. No. 08/484,654, Gardiner et al., filed Jun. 7, 1995.

U.S. patent application Ser. No. 07/927,134, Zhang et al., filed Aug. 7, 1992.

U.S. patent application Ser. No. 07/549,389, Kirlin et al., filed Jul. 7, 1990.

R.L. VanHermert, et al., J. Electrochemical Soc. (112), pp. 1123–1126, (1965) no month provided.

A. Reisman, J. Electrochemical Soc., vol. 136, No. 11, pp. 3525–3529 (Nov. 1989).

A. E. Kaloyeros, et al., J. Electronic Materials, vol. 19, No. 3, pp. 271–276 (1990) no month provided.

C. Oehr, et al., Applied Phys. A. (45), pp. 151–154 (1988) no month provided.

Houle, et al., Appl. Phys. Lett. (46) pp. 204–206 (1985); no month provided.

Awaya, et al., Conf. Proc., VLSI–VII (1992) no month provided; MRS, p. 345.

Girolami, et al., Chem. Mater. (1) pp. 8–10 (1989) no month provided.

Norman, et al., "New OMCVD Precursors for Selective Copper Metalization" Journal De Physique IV, Colloque C2, suppl. Au Journal de Physique II, vol. 1, 271–278, (Sep. 1991).

* cited by examiner

Primary Examiner—David Brunsman
(74) Attorney, Agent, or Firm—Margaret Chappuis; Steven J. Hultquist

(57) ABSTRACT

Compositions useful for chemical vapor delivery (CVD) formation of copper layers in semiconductor integrated circuits, e.g., interconnect metallization in semiconductor device structures, as an adhesive seed layer for plating, for the deposition of a thin-film recording head or for circuitization of packaging components. The copper precursor formulation may include one or more copper precursors, e.g., a precursor of the formula hfac(Cu)L where L is a low-cost ligand such as an alkene and/or alkyne such as [(hfac)Cu]$_2$ (DMDVS). The formulation may include in addition to the copper precursor(s) one or more low-cost ligand species such as alkenes, alkynes, dienes and combinations thereof, to increase thermal stability of the formulation and provide enhanced vaporization properties for CVD.

2 Claims, 4 Drawing Sheets

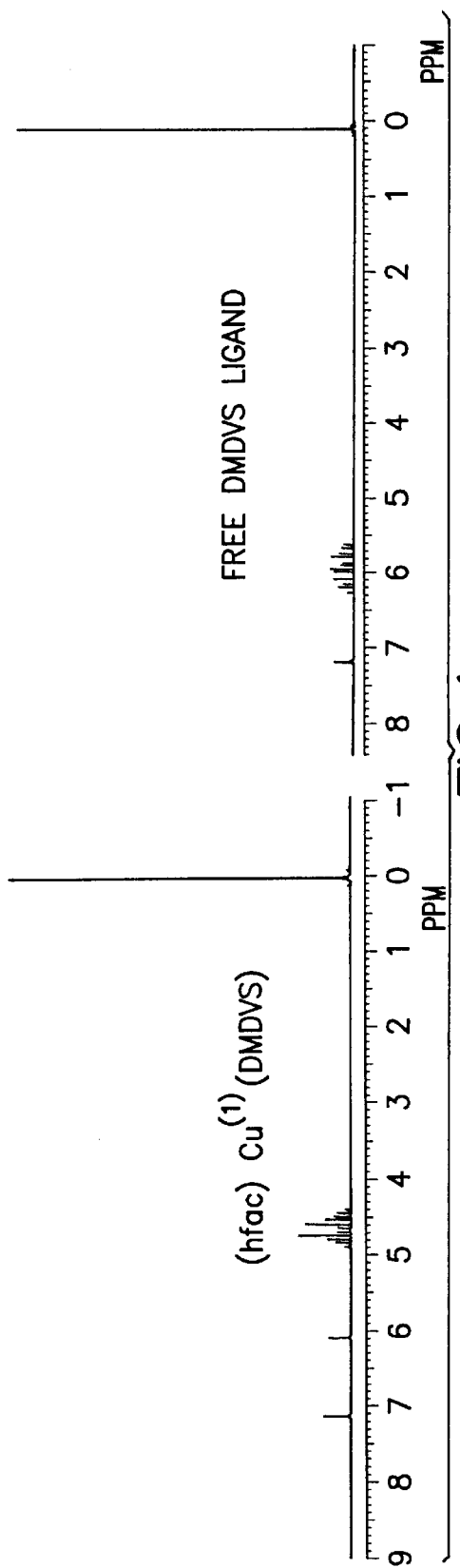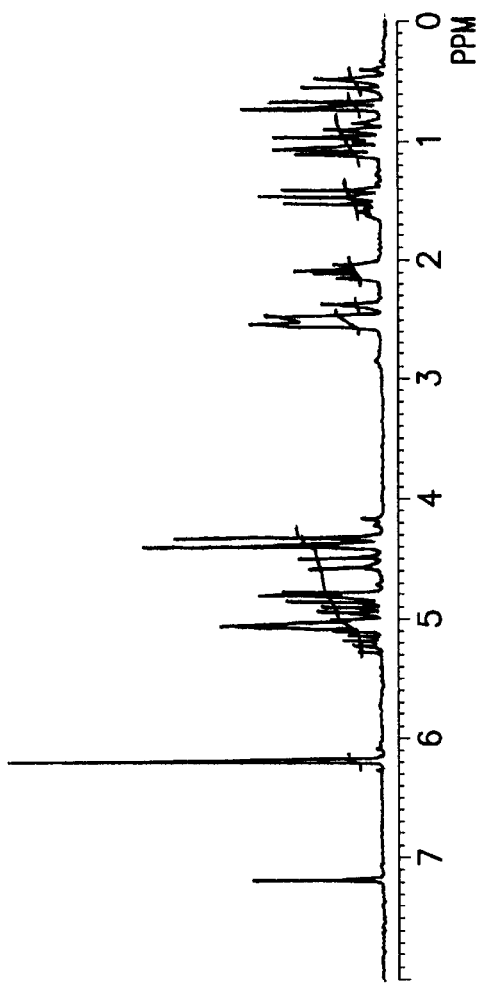

COMPOSITION AND PROCESS FOR PRODUCTION OF COPPER CIRCUITRY IN MICROELECTRONIC DEVICE STRUCTURES

BACKGROUND OF THE INVENTION

1. Field of the Invention

The present invention relates to copper precursor compositions and their synthesis, and to a method for production of copper circuits in microelectronic device structures, as for example in formation of metal interconnects for the manufacture of semiconductor integrated circuits, thin-film recording heads and packaging components, or otherwise for metallizing or forming copper-containing films on a substrate by metalorganic chemical vapor deposition (MOCVD) utilizing such precursor compositions. The precursor compositions of the invention are also usefully employed for forming seed layers of copper for subsequent electroless or electrochemical plating of copper and other metals.

2. Description of the Related Art

The process of fabricating semiconductor integrated circuits generally includes the formation of metal interconnect lines. The metal interconnect lines often may be formed from multiple conductive layers. For example, a thin conductive layer generally termed a barrier layer may be formed from a metal, metal nitride, metal silicide, or metal silicon nitride and a thicker conductive layer, e.g., composed of aluminum, may be formed on the barrier layer.

In order to enhance circuit speed performance and reduce the resistance-capacitance (RC) signal delay, the use of copper layers has been proposed and implemented to replace the use of aluminum layers, wherein one or more metal layers of a semiconductor integrated circuit may be formed utilizing a copper based layer. Copper is of great interest for use in metallization of VLSI devices because of its low resistivity, low contact resistance, and ability to enhance device performance through the reduction of RC time delays. Many semiconductor device manufacturers are adopting copper metallization for use in production of microelectronic chips, thin-film recording heads and packaging components.

Chemical vapor deposition (CVD) of copper provides uniform coverage for the metallization. Liquid CVD precursors and/or solid precursors dissolved into solvents or excess ligands enable direct injection and/or the liquid delivery of precursors into a CVD vaporizer unit. The accurate and precise delivery rate can be obtained through volumetric metering to achieve reproducibility in CVD metallization of in VLSI device manufacturing.

Currently only a few liquid copper precursors are commercially available. These include (hfac)Cu(MHY), (hfac)Cu(3-hexyne), (hfac)Cu(DMCOD) and (hfac)Cu(VTMS), wherein hfac=1,1,1,5,5,5-hexafluoroacetylacetonato, MHY=2-methyl-1-hexen-3-yne, DMCOD=dimethylcyclooctadiene, and VTMS=vinyltrimethylsilane.

In order to prevent detrimental effects which may be caused by the interaction of a copper layer with other portions of the integrated circuit, a barrier layer is typically utilized in conjunction with copper layers. Any of a wide range of barrier materials may be utilized including materials comprising metals, metal nitrides, metal suicides, and metal silicon nitrides. Exemplary barrier materials include titanium nitride, titanium silicide, titanium silicon nitrides, niobium nitrides, niobium silicon nitrides, tantalum nitride, tantalum silicide, tantalum silicon nitrides, tungsten nitride, tungsten silicide and tungsten silicon nitride. After the formation of a barrier layer, the copper is deposited on the barrier layer. The initial copper deposition may function as an adhesion seed layer, an electrochemical or CVD seed layer, and the initial copper deposition may be followed by electrochemical plating or CVD of copper. Alternatively, the copper deposition may be employed to fully deposit the desired amount or thickness of copper.

The use of various copper precursors in CVD reactors to create copper interconnects in semiconductor integrated circuits, for example, is well known. See, for instance, U.S. Pat. Nos. 5,085,731; 5,098,516; 5,144,049; and 5,322,712; and the references cited in those patents. New and useful compositions and processes for the production of copper that improve on, or provide alternatives to, these known compositions would be highly desirable and embody a significant advance in the art.

In this respect, copper CVD processes suitable for large-scale manufacture of integrated circuits are extremely valuable to the electronics industry. Towards these ends, copper CVD can be used in two ways:

1. deposition of an adherent and conductive thin-film layer as a plating base for electroplating processes.
2. full-fill deposition of copper interconnects, thin-film circuitry, recording head coils and other features.

In electroplating applications, several critical features must be achieved in the deposition of the plating base, or "seed" layer, for the subsequent electroplating to be successful. The deposition of a useful "thin-film seed layer" must satisfy the following film requirements:

1. The film requires low resistivity and uniform thickness, thereby allowing uniform current densities to be realized during plating.
2. The film requires uniform conformality in high aspect ratio features to satisfy complex device geometries, multi-level metal layers and damascene processing.
3. The film must exhibit excellent adhesion between the deposited copper metallurgy and the barrier layer, and between subsequent levels of metal interconnect metallurgy.

In an attempt to achieve these results, copper precursor alternatives to the current commercial materials, such as (hfac)Cu(vinyltrimethylsilane), commercially available as CupraSelect (Schumacher Division of Air Products & Chemicals, Inc., Allentown, Pa.) are badly needed. (Hfac)Cu(vinyltrimethylsilane), suffers from inherent thermal instability and therefore requires additives to enhance the molecule's physical properties, including thermal stability, and to facilitate uniform nucleation and film growth. Further, these chemical additives can induce process complexities and negatively alter device integration, such as by creating high contact resistances due to contamination of contacting surfaces (with fluorine and/or oxygen impurities).

For example, one additive that has been employed is hexafluoro-2,4-pentanedionate hydrate. The addition of such a hydrate to the vinyltrimethylsilane Cu(hfac), or corresponding addition of small amounts of water, has generally been found to substantially increase the deposition rate of the CVD process. Such additives, however, may lead to contamination of the interfacial surface regions and/or copper film, either during nucleation or steady-state film growth. In both cases, the electrical properties of the film or contact region may be compromised, resulting in high film resistivity and/or high contact resistance. In multi-layered structures, both of these electrical properties are critical in respect to device integration and manufacture.

Such contamination of the product film incident to the use of hfac-hydrate in the CVD formulations is attributable to the fact that hfac is susceptible to decomposition during the film growth process especially at the barrier-copper interface. In fact, Hhfac has been used to attack and etch metal surfaces, showing a strong tendency to remain on the surface of the barrier layer and/or copper nucleation layer during subsequent metallization. In addition, over time precursors such as vinyltrimethylsilane Cu(hfac) show decomposition to green Cu(II) species. Thus, the inherent thermal instability of this precursor and the required chemical additives pose significant deficiencies in the prior and current art. There is, therefore, a significant need in the art for copper formulations that deliver improved copper precursors to the CVD process without undesirable side effects. There is particularly a need for formulations that exhibit greater thermal stability without undesirable side effects due to the presence of fluorine substituents and/or aging of the precursor solution.

Alternative commercial alkyne and ene-yne Cu(I)(hfac) precursors are volatile and afford rapid deposition rates, but these compounds are also susceptible to thermal decomposition during heating, and they may form dinuclear complexes with decreased thermal stability and/or volatility. In both cases, the deposition rate may drop and hinder the ability to achieve "full-fill" metallization, so that the utility of these precursors is diminished for full-scale manufacturing of copper interconnects and copper-based devices. A method is therefore desired to circumvent this deficiency in the provision of improved precursors and formulations that are amenable to liquid delivery CVD.

Additionally, currently available precursors for copper CVD are quite expensive. To reduce the cost of copper metallization, inexpensive precursors need to be developed. In this regard, low cost ligands are required to lower the cost-of-ownership (COO) and provide an economic capability for manufacturing copper-based devices.

There is therefore a need in the art for new and improved copper precursors for metallization in the manufacture of integrated circuits and other microelectronic device structures, and for manufacturing thin-film recording heads, copper circuitry and packaging components, using techniques such as chemical vapor deposition, plasma-assisted CVD, plating, etc.

It is accordingly an object of the present invention to provide new copper precursors and formulations.

It is another object of the invention to provide methods of forming copper in the manufacturing of integrated circuits and other microelectronic device structures.

It is a further object of the invention to provide metallization technology for forming interconnects and other device structures that overcome the shortcomings and limitations of the prior art, including improved adhesion, improved contact resistances, improved film resistivities and improved device integration.

It is another object of the invention to provide a method of metallizing or forming copper-containing films on a substrate by metalorganic chemical vapor deposition (MOCVD) utilizing such novel copper precursor compositions.

It is a further object of the invention to provide adherent thin-films for seeding electroless and/or electrochemical plating solutions and to overcome the shortcomings and limitations of the prior art, including improved adhesion, improved contact resistances, improved films resistivities, improved plating, improved conformality, improved manufacturing, and improved device integration.

Other objects and advantages of the present invention will be more fully apparent from the ensuing disclosure and appended claims.

SUMMARY OF THE INVENTION

The present invention comprises a variety of aspects, features and embodiments, as will be more fully apparent from the ensuing disclosure and appended claims.

One aspect of the invention relates to a novel copper precursor composition hfac(Cu)$L_x$, wherein x is selected from the group consisting of ½ and 1 and L is a low-cost ligand selected from the group consisting of alkene, alkyne and combinations thereof.

Another aspect of the invention relates to a novel precursor composition formulation, including a novel copper precursor composition, having the formula (hfac)Cu(L)$_x$, wherein x is selected from the group consisting of ½ and 1 and L is a low-cost ligand selected from the group consisting of alkene, alkyne and combinations thereof, in formulation with one or more low-cost ligands selected from the group consisting of alkenes, alkynes, dienes and combinations thereof, to provide increased thermal stability to the formulation and improved vaporization to the CVD reactor.

Compositions of the invention provide unexpected improvements, e.g., increase in deposition rate, improvement in quality of copper, improved thin-film adhesion, reduction in copper impurities, reduction in problems associated with copper precursor decomposition that may detrimentally occur during delivery and transport to the reactor e.g., Cu(I) precursors to Cu(II) compounds, etc.

In another respect, the invention relates to a process for the production of copper, comprising subjecting a precursor composition to chemical vapor deposition, wherein the precursor composition comprises a novel copper precursor having the formula (hfac)Cu(L)$_x$, wherein x is selected from the group consisting of ½ and 1 and L is selected from the group consisting of alkene, alkyne and combinations thereof.

In another respect, the invention relates to a process for the production of copper, comprising subjecting a precursor formulation, to chemical vapor deposition, wherein the precursor formulation comprises a novel copper precursor in formulation with one or more low-cost additives, selected from the group consisting of alkene, alkyne, diene and combinations thereof, to provide increased thermal stability to the formulation.

Other aspects of the invention relate to the copper made by the process of this invention as well as integrated circuits, thin-film recording heads and/or packaging components made using the process of this invention.

The precursor compositions of this invention are usefil for the manufacture of copper, including copper interconnects for integrated circuits, thin-film recording heads and/or packaging components.

A further aspect of the invention relates to [(hfac)Cu]$_2$(DMDVS), and to a method of forming copper by vaporizing [(hfac)Cu]$_2$(DMDVS) (wherein DMDVS= dimethyldivinylsilane), as well as to a method of forming a seed layer comprising liquid injection or direct liquid vaporization of [(hfac)Cu]$_2$(DMDVS). In a further method aspect, the invention contemplates a method of making [(hfac)Cu]$_2$(DMDVS), comprising at least one of the following reactions (1) and (2):

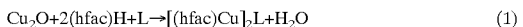

$$Cu_2O+2(hfac)H+L \rightarrow [(hfac)Cu]_2L+H_2O \qquad (1)$$

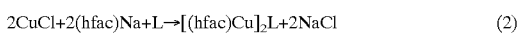

$$2CuCl+2(hfac)Na+L \rightarrow [(hfac)Cu]_2L+2NaCl \qquad (2)$$

wherein L is DMDVS. Interestingly, when using the DMDVS ligand, hfac may be replaced with tfac, wherein tfac is 1,1,1-trifluoroacetylacetonate, or other lower cost β-diketonate ligand. This approach is advantageous for reducing the potential for fluorine contamination by reducing the number of fluorine atoms in the precursor molecule. This achievement of a useful, economic copper precursor having a relatively low fluorine content is a further feature and advantage of this invention.

A further aspect of the invention relates to [(hfac)Cu]$_2$(DMDVS) in formulation with one or more low-cost additives, selected from the group consisting of, alkene, alkyne, diene and combinations thereof, to provide increased thermal stability to the formulation.

Another aspect of the invention relates to a method of forming a plating base or seed layer on a substrate for subsequent electroplating, comprising depositing on the substrate a layer of copper-containing material by liquid delivery chemical vapor deposition using a liquid-phase copper precursor that is thermally stable at liquid delivery vaporization temperatures, to form the layer of copper-containing material as the plating base seed layer.

A still further aspect of the invention relates to a microelectronic device structure comprising a substrate having a chemical vapor deposited copper plating base seed layer on the substrate, wherein the copper plating base seed layer has been formed using a liquid-phase copper precursor that is thermally stable at vaporization temperatures.

Another aspect of the invention relates to a method of full-fill copper metallization of a microelectronic device structure, comprising liquid delivery chemical vapor deposition of copper on the microelectronic device structure. The copper precursor for such full-fill metallization, may therefore comprise a novel copper precursor of the formula (hfac)Cu(L)$_x$, wherein x is selected from the group consisting of ½ and 1 and L is a ligand selected from the group consisting of alkene, alkyne and combinations thereof. Specific examples of alkyne ligands embodied in the current invention include, but are not limited to ene-yne, diyne, diene-yne, amine-yne, keto-yne and alkyne. Such novel precursor compositions may be used alone or in formulation with a low cost stabilizer additive selected from the group consisting of alkene, alkyne, diene and combinations thereof.

Yet another aspect of the invention relates to a formulation including the novel copper precursor composition (hfac)Cu(L)$_x$, described hereinabove, in formulation with an additive, wherein the additive provides added thermal stability and comprises a low cost ligand selected from the group consisting of:

(a) alkenes:

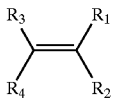

wherein $R_1$, $R_2$, $R_3$ or $R_4$ may be the same as or different from one another, and are independently selected from H, aryl, perfluoroaryl, $C_1$–$C_8$ alkyl or open-chain alkyl, $C_1$–$C_8$ perfluoroalkyl, and $C_5$–$C_6$ cycloalkyl;

(b) alkynes:

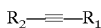

wherein $R_1$, and $R_2$ may be the same or different and are independently selected from H, aryl, perfluoroaryl, $C_1$–$C_8$ alkyl, $C_1$–$C_8$ perfluoroalkyl, vinyl, and $C_1$–$C_6$ cyclo-alkyl;

(c) dienes:

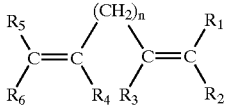

wherein $R_1$, $R_2$, $R_3$, $R_4$, $R_5$ and $R_6$ may be the same or different and are independently selected from H, and $C_1$–$C_3$ alkyl and wherein n=0, 1,2,3 or 4;and (d) combinations of the foregoing, e.g., alkene, alkyne, diene, keto-yne, etc.

A further aspect relates to a method of forming copper thin films comprising vaporizing a precursor formulation comprising a novel copper precursor composition (hfac)Cu(L)$_x$, wherein x is selected from the group consisting of ½ and 1 and L is a low cost ligand selected from the group consisting of alkene, alkyne and combinations thereof, in formulation with an additive of the above-described type.

A still further aspect of the invention relates to a novel copper precursor formulation comprising a novel copper precursor composition selected from the group consisting of (A) [(hfac)Cu]$_2$(DMDVS);
(B) [(tfac)Cu]$_2$(DMDVS);
(C) (hfac)Cu(DMCOD)
(D) (hfac)Cu(MHY); and
(B) (hfac)Cu(L)x wherein x is selected from the group consisting of ½ and 1 and L is a low-cost ligand selected from the group consisting of alkene, alkyne and combinations thereof, in formulation with a low-cost additive selected from the group consisting of:

(I) alkenes:

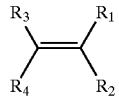

wherein $R_1$, $R_2$, $R_3$ or $R_4$ may be the same as or different from one another, and are independently selected from H, aryl, fluoroaryl, perfluoroaryl, $C_1$–$C_8$ alkyl or open-chain alkyl, $C_1$–$C_8$ fluoroalkyl, $C_1$–$C_8$ perfluoroalkyl, and $C_5$–$C_6$ cycloalkyl;

(II) alkynes of the formula:

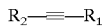

wherein $R_1$, and $R_2$ may be the same or different and are independently selected from H, aryl, fluoroaryl, perfluoroaryl, $C_1$–$C_8$ alkyl, $C_1$–$C_8$ fluoroalkyl, $C_1$–$C_8$ perfluoroalkyl, vinyl, and $C_5$–$C_6$ cycloalkyl;

(III) dienes of the formula:

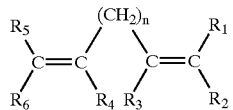

wherein $R_1$, $R_2$, $R_3$, $R_4$, $R_5$, and $R_6$ may be the same or different and are independently selected from H, and $C_1$–$C_3$ alkyl and wherein n=0, 2, 3 or 4; and (IV) combinations of the foregoing, e.g., alkene, alkyne, diene, keto-yne, etc.

Another aspect of the invention relates to a method of forming a copper-containing material on a substrate, comprising vaporizing a copper precursor composition or formulation to form a precursor vapor, and contacting the precursor vapor with a substrate to form the copper-containing material thereon.

Other aspects and features of the invention will be more fully apparent from the ensuing disclosure and appended claims.

BRIEF DESCRIPTION OF THE DRAWINGS

FIG. 1 is a $^1$H NMR spectrum of [(hfac)Cu]$_2$(DMDVS) (left side of spectrum) and of DMDVS (right side of spectrum) in $C_6D_6$.

FIG. 2 is an $^1$H NMR spectrum of [(hfac)Cu]$_2$(5-vinyl-2-norborene).

DETAILED DESCRIPTION OF THE INVENTION, AND PREFERRED EMBODIMENTS THEREOF

Figure 3:
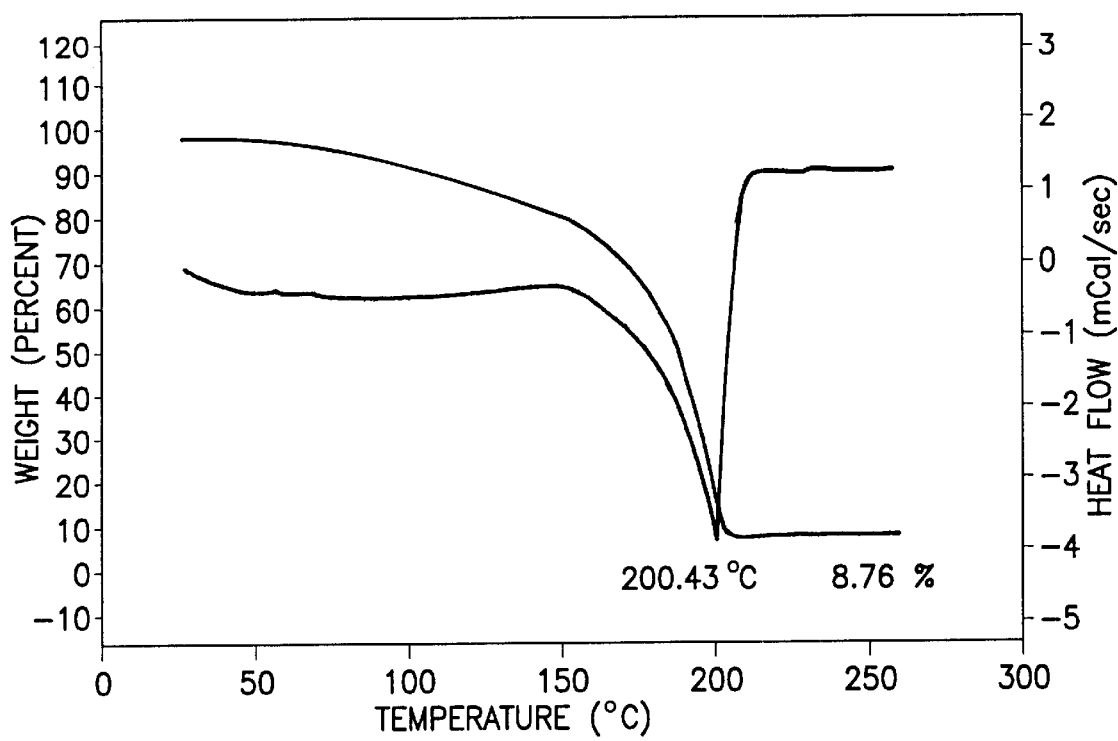
FIG. 3 is a graph of the thermal analysis of [(hfac)Cu]$_2$ (5-vinyl-2-norborene).

Copper precursors that may variously be used in the broad practice of this invention include, but are not limited to, the copper compounds and complexes described in U.S. Pat. Nos. 5,085,731; 5,094,701; 5,098,516; 5,144,049; 5,322,712; 3,356,527; and 3,594,216 and the copper compounds and complexes variously described in R. L. VanHemert et al., J. Electrochemical Soc. (112), 1123 (1965); Reisman et al., J. Electrochemical Soc., Vol. 136, No. 11, (November 1989); A. E. Kaloyeros et al., J. electronic materials, Vol. 19, No. 3, p. 271 (1990); Oehr H. Suhr, Applied Phys. A. (45) 151–154 (1988); Houle et al., Appl Phys. Lett. (46) pp. 204–206 (1985); Awaya et al., Conf. Proc., VLSI-VII (1992); MRS, p. 345; Girolami et al., Chem. Mater. (1) pp. 8–10 (1989); and Norman et al., E-MRS Proc. B17, pp. 87–92 (1993), the entire contents of which are hereby incorporated herein by reference.

Non-limiting, representative copper precursors include Cu(II)bis(acetylacetonate), Cu(II)bis(hexafluoracetylacetonate) (i.e., (Cu(II)(hfac)$_2$), Cu(I) hfac.2-methyl-1-hexen-3-yne ("Cu(I)hfac(MHY)" or "(hfac)Cu(MHY)"), Cu(I)hfac(trimethylvinylsilane) ("(hfac)Cu TMVS") and copper complexes of formula I: Cu$^{+1}$(R$^1$—CO—CR$^2$—CO—R$^3$)$^{-1}$[C(R$^4$)(R$^5$)=C(R$^5$)Si (R$^6$)$_3$] wherein R$^1$ and R$^3$ are each independently C$_1$–C$_8$ perfluoroalkyl, R$^2$ is H$_1$, F or C$_1$–C$_8$ perfluoroalkyl, R$^4$ is H$_1$ C$_1$–C$_8$ alkyl, or Si(R$^6$)$_3$ each R$^5$ is independently H or C$_1$–C$_8$ alkyl, and R$^6$ is independently phenyl or C$_1$–C$_8$ alkyl.

The complexes of formula I may be made using the procedures set forth in U.S. Pat. No. 5,144,049 and references cited therein.

Apart from the foregoing, the disclosures of the following United States patents and patent applications are hereby incorporated herein by reference in their entireties:

U.S. patent application Ser. No. 08/835,768 filed Apr. 8, 1997 in the names of Thomas H. Baum, et al.;

U.S. patent application Ser. No. 08/484,654 filed Jun. 7, 1995 in the names of Robin A. Gardiner et al.;

U.S. patent application Ser. No. 08/414,504 filed Mar. 31, 1995 in the names of Robin A. Gardiner et al.;

U.S. Application Ser. No. 08/280,143 filed Jul. 25, 1994, in the names of Peter S. Kirlin, et al.;

U.S. patent application Ser. No. 07/927,134, filed Aug. 7, 1992 in the same names;

U.S. patent application Ser. No. 07/807,807, filed Dec. 13, 1991 in the names of Peter S. Kirlin, et al., now issued as U.S. Pat. No. 5,204,314;

U.S. Application Ser. No. 08/181,800 filed Jan. 15, 1994 in the names of Peter S. Kirlin, et al., and issued as U.S. Pat. No. 5,453,494;

U.S. Application Ser. No. 07/918,141 filed Jul. 22, 1992 in the names of Peter S. Kirlin, et al., and issued Jan. 18, 1994 as U.S. Pat. No. 5,280,012;

U.S. Application Ser. No. 07/615,303 filed Nov. 19, 1990;

U.S. application Ser. No. 07/581,631 filed Sep. 12, 1990 in the names of Peter S. Kirlin, et al., and issued Jul. 6, 1993 as U.S. Pat. No. 5,225,561; and U.S. patent application Ser. No. 07/549,389 filed Jul. 6, 1990 in the names of Peter S. Kirlin, et al.

Further, such copper precursor compositions may be substantially devoid of:

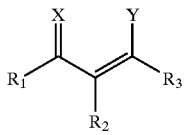

wherein R$_1$, and R$_3$, are independently selected from alkyl, aryl, fluoroalkyl or fluoroaryl; R$_2$ is halogen, alkyl, aryl, fluoroalkyl, or fluoroaryl; X and Y are selected such that when X=O, Y is OH, NH$_2$ or N(R$_4$)H, when X=NH, Y is NH$_2$ or N(R$_4$)H, when X=NR$_5$, Y is (R$_4$)H, and R$_4$ and R$_5$ are selected from the group consisting of alkyl, aryl, fluoroalkyl and fluoroaryl.

In general, the copper precursor compositions of the invention may be formulated to comprise, consist of, or consist essentially of any appropriate components herein disclosed, and such copper precursor compositions of the invention may additionally, or alternatively, be formulated to be devoid, or substantially free, of any components taught to be necessary in prior art formulations that are not necessary to the achievement of the objects of the invention hereunder.

The compositions of the present invention as described hereinabove may be useful in a number of applications. For example, the compositions may be used during the formation of copper interconnect lines in semiconductor integrated circuitry, thin-film circuitry, thin-film packaging components and thin-film recording head coils. To form such integrated circuitry or thin-film circuitry, a semiconductor substrate may be utilized having a number of dielectric and conductive layers (multilayers) formed on and/or within the substrate.

As used herein the semiconductor substrate may include a bare substrate or any number of constituent layers formed on a bare substrate.

In the broad practice of the present invention, a copper-containing layer may be formed on a semiconductor substrate for use in a first, second, third, or more metallization layer. Such copper layers typically are used in circuit locations requiring low resistivity and/or high speed circuit paths. As discussed in the background section hereof, before a copper layer is formed on a semiconductor substrate, a barrier layer may be deposited or otherwise formed on the substrate.

The copper precursor compositions described herein may then be deposited on the wafer using a CVD system. Metalorganic CVD (MOCVD) systems may be utilized for such purpose, such systems being well known in the semiconductor fabrication art. MOCVD systems potentially useful in the broad practice of the invention include atmospheric pressure MOCVD systems as well as low (or reduced) pressure MOCVD systems.

The compositions of the present invention are not limited in respect of their use with such deposition tools, however, and other CVD tools, for example PECVD tools, or other deposition tools, may be utilized. Further, water or water-generating compounds may be mixed with the copper precursor upstream of, or within, the CVD tool.

The compositions of the present invention may be delivered to the CVD reactor in a variety of ways. For example, a liquid delivery system may be utilized. Such systems generally include the use of liquid MFCs (mass flow controllers). An exemplary liquid delivery system useful in the general practice of the invention is the ADCS Sparta 150 Liquid Delivery System (commercially available from ATMI, Inc., Danbury, Conn.).

Liquid delivery systems generally meter a desired volumetric quantity of a liquid to achieve a uniform flow rate of the precursor composition to the CVD process tool. At the process tool chamber the liquid may be vaporized through use of a vaporizer or a transducer activated by ultrasound or acoustic techniques. Various configurations and types of liquid delivery systems are described in U.S. Pat. Nos. 5,204,314; 5,362,328; 5,536,323; and 5,711,816, the disclosures of which are hereby expressly incorporated herein by reference in their entireties.

In liquid delivery formulations, copper precursor formulations of the invention may include solvent component(s) of suitable character as may be desirable and advantageous in a given end use application to form copper on a substrate. Solvents may for example include alkane solvents, e.g., octane, or aryl solvents such as benzene or toluene. It is generally desirable to avoid oxo (—O—) solvents such as ethers as solvent species in the copper precursor formulations of the invention.

The use of the compositions disclosed herein is not limited to liquid delivery systems, and any method that adequately delivers the precursor composition to the process may be usefully employed. Thus, for example, bubbler-based delivery systems may be utilized. In such systems, an inert carrier gas may be bubbled through the precursor composition to provide a resulting gas, which is wholly or partially saturated with the vapor of the precursor composition, for flow to the CVD tool.

A wide variety of CVD process conditions may be utilized with the precursor compositions of the present invention. Generalized process conditions may include substrate temperature ranges of 150–400° C., with about 190° C. to about 200° C. being more typical; vaporizer temperature ranges of about 50 to about 100° C., with 65° C. being more typical; pressure ranges of 0.05–5 Torr (and most preferably about 0.5 Torr), with a range of about 0.2 to about 0.5 Torr being more typical; and inert gas flows of helium, nitrogen, or argon at 25–750 sccm (and most preferably 100 sccm) at a temperature of approximately the same as the vaporizer.

The present invention in one aspect involves the use of a novel copper precursor composition (hfac)Cu)L$_x$, as a source reagent for the deposition of copper, wherein x is selected from the group consisting of ½ and 1 and L is a low-cost ligand selected from the group consisting of alkene, alkyne and combinations thereof. The low cost ligands L may be derived from ligand source compounds having a price that in year 2000 U.S. dollars is less than $1.00 US/gram, with preferred low cost levels being less than $0.75 US/gram and more preferred low cost levels being at commodity chemical prices less than $0.50 US/gram.

The invention also contemplates novel precursor composition formulations, including one or more novel copper precursor compositions of the aforementioned type, having the formula (hfac)Cu(L)$_x$, wherein x is selected from the group consisting of ½ and 1and L is a low-cost ligand selected from the group consisting of alkene, alkyne and combinations thereof, in formulation with one or more low-cost ligands selected from the group consisting of alkenes, alkynes, dienes and combinations thereof, to provide increased thermal stability to the formulation and improved vaporization to the CVD reactor.

The invention thus relates in one aspect to the use of formulations containing one or more copper precursor compositions, which are stabilized in formulation with one or more low-cost ligands selected from the group consisting of alkenes, alkynes, dienes and combinations thereof.

The following examples are representative of specific aspects of the invention and are not intended to limit the scope of the invention or claims hereto.

As used herein, "MHY" means 2-methyl-1-hexen-3-yne. The Cu(I)hfac(MHY) precursor was prepared using standard techniques.

EXAMPLE I

A mixture of (hfac)Cu(DMCOD) with approximately 1% of 1-hexene was well-shaken, then set at room temperature under a nitrogen atmosphere. After one month, no decomposition was observed. The copper composition was suitable for liquid delivery or direct liquid injection into the CVD chamber for vaporization thereof.

EXAMPLE II

A mixture of (hfac)Cu(MHY) with approximately 2% of 1-hexene was well-shaken, then set at room temperature under a nitrogen atmosphere. After two months, no decomposition was observed and the resultant copper composition was suitable for liquid delivery or direct liquid injection into the CVD chamber. The 1-hexene provided a low cost stabilizer for increasing the thermal stability of the copper precursor composition during storage and vaporization.

EXAMPLE III

A mixture of (hfac)Cu(VTMS) with approximately 2% of 1-hexene was well-shaken, then set at room temperature under a nitrogen atmosphere. After a week, no decomposition was observed and the copper composition was suitable for liquid delivery or direct liquid injection into the CVD chamber. The 1-hexene provided a low cost stabilizer for increasing the thermal stability of the copper precursor composition during storage and subsequent vaporization.

EXAMPLE IV

A mixture of solid (hfac)Cu(MHK) with approximately 50% of 1-hexene was well-shaken, then set at room temperature under a nitrogen atmosphere. After 3 months, no decomposition was observed and the copper composition was suitable for liquid delivery or direct liquid injection into the CVD chamber. In another experiment, a mixture of (hfac)Cu(MHK) with approximately 50% of pentane was well-shaken and then set at room temperature under a nitrogen ambient. Decomposition was observed within one hour and the mixture turned a blue color. Obviously, the 1-hexene provided a low cost stabilizer for increasing the thermal stability of the copper precursor composition during storage and subsequent vaporization.

EXAMPLE V

A mixture of (hfac)Cu(DVDMS) with approximately 2% of 1-hexene was well-shaken, then set at room temperature under a nitrogen atmosphere. After a week, no decomposition was observed and the copper composition was suitable for liquid delivery or direct liquid injection into the CVD chamber. The 1-hexene provided a low cost stabilizer for increasing the thermal stability of the copper precursor composition during storage and subsequent vaporization.

Because the compositions disclosed herein are stable, these compositions provide advantageous features. For example, these compositions may be formulated by a chemical supplier prior to shipment to the end user, due to their stable characteristics. The inventive composition may then be supplied to a CVD tool within a single liquid supply line.

Co-injection of a water vapor to the CVD process reactor can be used to enhance the film growth rate and alter the CVD process. In this manner, a stable copper-bearing composition is provided which may simplify the end user's CVD process operation.

In another aspect of the present invention, the use of a thermally stable copper precursor, such as (dimethyl-1,5-cyclooctadiene)Cu(I)(hfac), or the use of a low-cost, alkene-stabilized (hfac)Cu)L$_x$, provides a distinct advantage for copper CVD, especially for the deposition of plating base layers. The enhanced thermal stability of these precursors eliminates the need for Hhfac additives to stabilize the compound. Further, the thermal stability of the precursor allows liquid delivery techniques to be used to achieve reproducible delivery, reproducible film growth and uniform deposition rates. The combined liquid delivery and enhanced thermal stability allows low volatility materials to be volumetrically delivered, leading to reproducible transport and deposition.

The utility of this approach for producing a conformal, thin-film with good electrical properties and high adhesion to the barrier layer (TiN or TaN) is an advantage of the present invention. The conformality of the deposited film is readily achievable through CVD techniques and thereby enables the extension of electroplating technologies to next-generation microelectronic device geometries and dimensions. For example, a conformal plating base required for such applications may involve 0.10 μm linewidths with 4–8:1 aspect ratio vias. The conformal deposition of these dimensions cannot be realized by currently available physical deposition methods. Thus, CVD offers a feasible and attractive pathway to future device generations in connection with current low-cost electroplating processes.

One preferred copper precursor in the practice of the present invention, (dimethyl-1,5-cyclooctadiene)Cu(I)(hfac), is a low vapor pressure liquid. As a consequence, the deposition of a plating base layer using such precursor requires only thin conductive films (i.e., 1000 Angstroms). The deposition process, therefore, can be relatively slow provided the electrical properties, the adhesion and the conformality are excellent. This is readily achieved by (dimethyl-1,5-cyclooctadiene)Cu(I)(hfac) since it requires no additives that may introduce impurities. Further, such precursor has demonstrated good resistivities and excellent conformality, as well as suitable adhesion on copper. Corresponding thermally stable, liquid precursors may be employed to produce similar results during the deposition of copper metal, as a means to deposit an electrically conducting plating base layer.

The use of liquid delivery to introduce alkyne and ene-yne copper precursors to the CVD reactor is, therefore, an enabling approach towards "full-fill" copper CVD. The liquid delivery approach allows the alkyne copper precursor to be at elevated temperatures for a very short time, thereby avoiding the loss of alkyne ligand (such loss being undesirable as leading to the formation of dinuclear species) and avoiding thermal decomposition of the precursor. The addition of a small amount of the alkene (i.e., 1-hexene) can also force the chemical equilibrium of the mixture towards the starting precursor during storage, vaporization and heating. Using both of these changes, in combination, is the preferred method for liquid delivery of the (L$_x$) copper (I)(hfac) precursors.

Other embodiments of this invention will be readily apparent to those of ordinary skill in the art, based on the disclosure herein. For example, the addition of water, Hhfac hydrate or other co-reactants may be advantageously employed. The copper precursors may for example comprise alkyne stabilized Cu(I)(hfac) species, wherein the alkyne is mono-substituted, di-substituted, or unsaturated (i.e., an ene-yne, a di-yne, diene-yne) or otherwise comprises alkyl substituted analogs of the precursor species of the foregoing examples.

The liquid delivery approach achieves reproducible film growth and uniform deposition rates. A combined liquid delivery and flash vaporization process may be employed, such as the LDS300 liquid delivery and vaporizer unit (commercially available from ATMI, Inc., Danbury, Conn.), to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD process.

The deposition of copper thin films with useful electrical properties (low resistivity) and good adhesion to the barrier layer (e.g., formed of TiN or TaN), is also achieved by the process and precursors of the present invention. The conformality of the deposited film is practically achievable only through CVD techniques which thereby provide a pathway to the achievement of "full-fill" copper metallization. The liquid delivery approach of the present invention, including "flash" vaporization and the use of copper precursor chemistry as herein disclosed, enable next-generation device geometries and dimensions to be attained, e.g., a conformal vertical interconnect of <0.13 micron linewidths with 4–8:1 aspect ratio. The conformal deposition of interconnects of these critical dimensions cannot be realized by currently available physical deposition methods. Thus, the approach of the present invention affords a viable pathway to future generation devices, and embodies a substantial advance in the art.

Other thermally stable, liquid precursors may be advantageously employed to produce similar results during the deposition of copper metal to form "full-fill" interconnects via CVD.

A further aspect of this invention relates to a liquid (hfac)Cu(L)$_x$ composition, wherein x is ½ and the ligand L is dimethyldivinylsilane. Such liquid composition is a highly advantageous precursor for liquid delivery chemical vapor deposition of copper. Further, when using this Lewis base ligand, the fluorine content can be reduced in the coordinated β-diketonate ligand. For example, DVDMS [Cu(tfac)]$_2$, wherein tfac is 1,1,1-trifluoro-2,4-pentanedionate, can be formed and exhibits useful stability.

The composition (hfac)Cu is unstable per se. It exists only in the adducted form (hfac)Cu)L$_x$, wherein x is selected from the group consisting of ½ and 1 and L is a neutral Lewis base ligand. (hfac)Cu)L$_x$, complexes when used for CVD of copper undergo a disproportionation reaction at elevated temperature, forming pure copper metal, free Lewis base ligand and Cu(hfac)$_2$, in accordance with the following equation:

$$2Cu(hfac)L_x \rightarrow Cu + Cu(hfac)_2 + 2L_x \qquad (1)$$

Such complexes can be synthesized either by reacting Cu$_2$O with Hhfac in the presence of Lewis base ligands or by reacting CuCl with (hfac)Na in the presence of Lewis base ligands, as illustrated by equations (2) and (3) below.

$$Cu_2O + 2(hfac)H + 2L_x \rightarrow 2(hfac)_x + H_2O \qquad (2)$$

$$CuCl + (hfac)Na + L_x \rightarrow (hfac)CuL_x + NaCl \qquad (3)$$

The synthesis and characterization of a liquid complex of [(hfac)Cu]$_2$(DMDVS) is described below. This complex provides better thermal stability than (hfac)Cu(VTMS), which as mentioned earlier herein suffers from poor thermal stability.

EXAMPLE VI

The general reactions were carried out under a steady flow of nitrogen. A Schlenk flask was charged with 3.4 grams of copper (I) oxide and 3.0 grams (27 mmol, 1.1 equivalent on the basis of hfacH) of dimethyldivinylsilane with 10 mL anhydrous methylene chloride. 1,1,1,5,5,5-hexafluoroacetylacetone (hfacH) (5.0 grams, 24 mmol) in 5 mL $CH_2Cl_2$ was added dropwise to the magnetically stirred suspension at about −5° C. After the addition, the suspension was stirred overnight at room temperature. Then the mixture was filtered through a neutral $Al_2O_3$ column. A light yellow filtrate was recovered. Removal of volatiles of the filtrate yielded 6.2 grams (about 70%) yellow mobile liquid. The yellow liquid was characterized by solution NMR. NMR $(C_6D_6)$, δ (ppm), $^1H$; 6.17 (s, 1H, C$\underline{H}$ of hfac), 4.3–4.9, (m, 6H, 2×C$\underline{H}$=C$\underline{H}_2$), 0.04 (s, 6H, 2×C$\underline{H}_3$); 13C; 178.3 (q, $\underline{C}$=O of hfac), 118.3 (q, $\underline{C}F_3$ of hfac), 111.3 (s, Si—CH=CH$_2$), 105.8 (s, Si—$\underline{C}$H=CH$_2$), 90.2 (s, $\underline{C}$H of hfac), −3.05 (s, $\underline{C}H_3$—Si).

A $^1H$ NMR spectrum of [(hfac)Cu]$_2$(DMDVS) is shown in FIG. 1, left side, at room temperature. The resonance of bonded vinyl protons shifts upfield significantly (about 1–3 ppm) compared to those of free ligand DMDVS, shown in the right hand portion of the spectrum of FIG. 1.

The precursor [(hfac)Cu]$_2$(DMDVS) is useful as a liquid precursor for the formation of copper, by liquid delivery CVD or other formation technique. A CVD process may be carried out using such precursor for copper metallization in the fabrication of integrated circuitry, or for formation of a copper seed layer by either liquid injection or direct vaporization.

The complexes can be synthesized by either reacting $Cu_2O$ and hfacH in the presence of Lewis base ligands or by reacting CuCl with (hfac)Na in the presence of Lewis base ligands, as illustrated in the following equations (2) and (3), respectively.

From $Cu_2O$:

$$Cu_2O + 2(hfac)H + 2L_x \rightarrow 2(hfac)_x + H_2O \quad (2)$$

From CuCl:

$$CuCl + (hfac)Na + L_x \rightarrow (hfac)CuL_x + NaCl \quad (3)$$

These (hfac)Cu(L)$_x$ complexes display good volatility and thermal stability and are excellent precursors for CVD of copper. The copper CVD precursors of such type that heretofore have been used for copper CVD comprise Lewis base ligands that are typically quite expensive in character. The present invention contemplates inexpensive Lewis base ligands including alkenes, dienes and alkynes, including the ligand source compound species set out in Table 1 below, together with boiling point (B.p.) data, and representative current prices of the ligand source compound species as commercially available.

TABLE 1

Ligand source compound species and price[1]

| Chemical ligand species | B.p. (° C.) | Price (U.S. dollars/gram) |
|---|---|---|
| 1-hexene | 64 | 0.02 |
| isoprene | 34 | 0.03 |
| 1-hexyne | 71–72 | 0.68 |
| 2-butyne | 27 | 0.50 |
| 5-vinyl-2-norbornene | 141 | 0.04 |
| 2,5-dimethyl-2,4-hexadiene | 132–134 | 0.09 |
| Dipentene | 170-80 | <0.01 |

[1] source: Aldrich Chemical Company 1998 Handbook of Fine Chemicals

An illustrative description of synthesis and characterization of some low cost (hfac)Cu(L)$_x$ complexes, wherein x is selected from the group consisting of ½ and 1 and L represents the low cost Lewis base ligand, is set out below.

These complexes are useful as copper CVD precursors, and the Lewis base ligand can be added as a thermal stabilizer to form useful copper compositions.

Synthesis and Characterization (hfac)Cu(1-hexene): The general reactions were carried out under a steady flow of nitrogen. A Schlenk flask was charged with 3.4 g of copper (I) oxide and 2.4 g (28 mmol, 1.2 equivalent on the basis of hfacH) of 1-hexene with 10 mL anhydrous methylene chloride. 1,1,1,5,5,5-hexafluoroacetylacetone (hfacH) (5.0 g, 24 mmol) in 5 mL $CH_2Cl_2$ was added dropwise to the magnetically stirred suspension at about −10° C. After the addition, the suspension was stirred for additional 24 hours at room temperature. Then the mixture was filtered through a neutral $Al_2O_3$ column. Light yellow filtrate was collected. Removal of volatiles of the filtrate gave 6 g (~70%) yellow liquid. The yellow liquid was characterized by solution $^1H$ NMR:

$^1H$ NMR $(C_6D_6)$, δ (ppm), 6.19 (s, 1H, C$\underline{H}$ of hfac), 4.40, (m, 1H, C$\underline{H}$=CH$_2$), 3.48–3.56 (m, 2H, CH=C$\underline{H}_2$), 1.48 (m, 2H, C$\underline{H}_2$—CH=CH$_2$), 1.07 (m, 2H, 2×CH2), 0.76 (m, 3H, C$\underline{H}_3$).

[(hfac)Cu]$_2$(5-vinyl-2-norborene): Yellow low melting point solid. Because the free ligand is composed of the endo- and exo-5-vinyl-2-norborene isomers, the $^1H$ NMR spectra are very complicated, as shown in FIG. 2.

Thermal analysis of [(hfac)Cu]$_2$(5-vinyl-2-norborene) is shown in FIG. 3. The weight loss before 150° C. may be attributed to the combination of evaporation of the compounds and the loss of the excess free ligand, e.g. 5-vinyl-2-norborene.

[(hfac)Cu]$_2$(2,5-dimethyl-2,4-hexadiene): Light yellow solid. $^1H$ NMR, δ$(C_6D_6)$: 1.37(s, 6H, 2×CH$_3$ of the diene), 1.60(s, 6H, 2×CH$_3$ of the diene), 4.93 (s, 2H 2×=CH of the diene), 6.09 (s, 2H, 2×CH of hfac).

Figure 4:
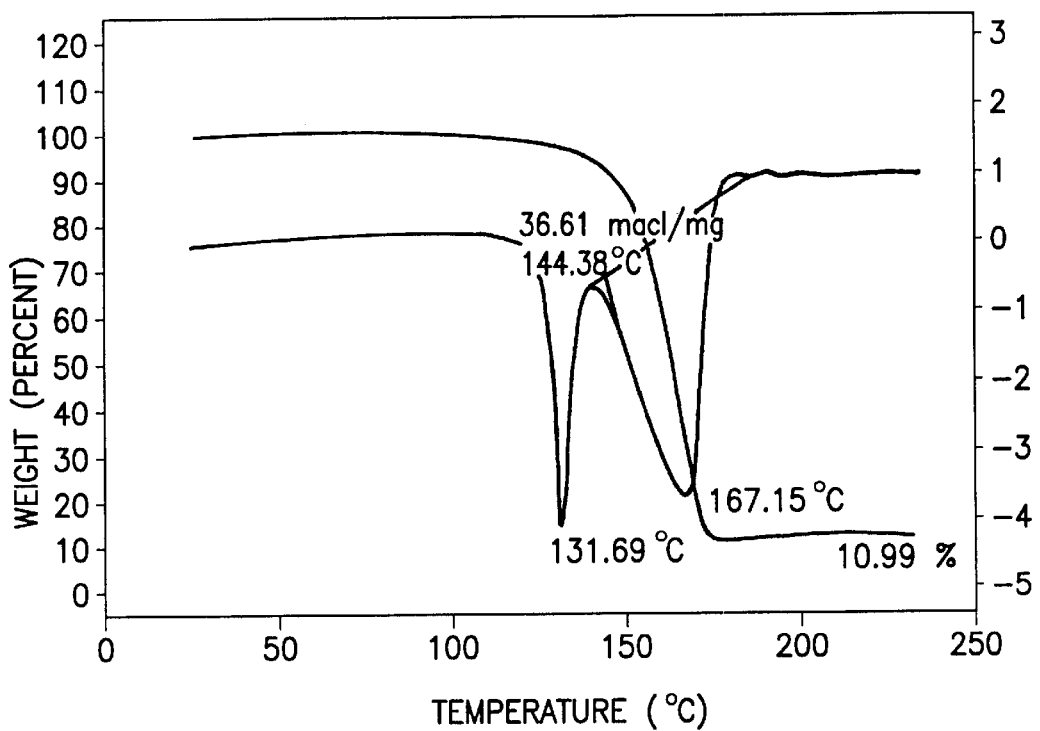
FIG. 4 is a graph of the thermal analysis of (hfac)Cu(2, 5-dimethyl-2, 4-hexadiene).

Thermal analysis of [(hfac)Cu]$_2$(2,5-dimethyl-2,4-hexadiene) is shown in FIG. 4. A melting endotherm peak was observed at 131° C.

The foregoing are illustrative of the novel, low cost (hfac)Cu(L)$_x$ complexes of the invention. The ligands used in these complexes are inexpensive, which reduces the production cost of these (hfac)Cu(L)$_x$ complexes significantly. Such complexes are useful as precursors of copper in CVD processes.

The invention thus contemplates a series of new and low cost (hfac)Cu(L)$_x$ complexes for use as precursors of copper CVD, where L can be alkene, alkyne or diene. In a related aspect of this invention, an additive may be used to stabilize the (hfac)Cu(L)$_x$ complex formulation, wherein the additive provides added thermal stability and comprises a low cost ligand selected from the group consisting of the respective species illustrated in Schemes 1 to 3 below.

Scheme 1.: Alkenes

The alkenes may be of the formula

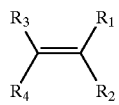

wherein $R_1$, $R_2$, $R_3$ or $R_4$ may be the same as or different from one another, and are independently selected from H, aryl, fluoroaryl, perfluoroaryl, $C_1$–$C_8$ alkyl or open-chain alkyl, $C_1$–$C_8$ fluoroalkyl, $C_1$–$C_8$ perfluoroalkyl, and $C_5$–$C_6$ cycloalkyl. Illustrative examples of such alkenes include 1-hexene, 1-pentene, 1-butene, 1-propene and others.

Scheme 2: Alkynes

The alkynes may be of the formula:

wherein $R_1$ and $R_2$ may be the same or different and are independently selected from H, aryl, fluoroaryl, perfluoroaryl, $C_1$–$C_8$ alkyl, $C_1$–$C_8$ fluoroalkyl, $C_1$–$C_8$ perfluoroalkyl, vinyl, and $C_5$–$C_6$ cycloalkyl. An illustrative example of such hexynes is 1-hexyne.

Scheme 3: Dienes

Dienes of such type include those of the formula:

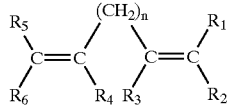

wherein $R_1$ $R_2$, $R_3$, $R_4$, $R_5$ and $R_6$ may be the same or different and are independently selected from H, and $C_1$–$C_3$ alkyl and wherein n=0, 1, 2, 3 or 4. An illustrative example of such dienes is 2,5-dimethyl-2,4-hexadiene.

Suitable dienes also include those with one or both carbon-carbon double bond(s) in one or two ring structure (s). Examples include 5-vinyl-2-norborene and dipentene (p-mentha-1,8-diene).

The foregoing copper precursors may be utilized in a CVD process for copper metallization or the formation of a copper seed layer via either liquid injection or direct vaporization.

In another aspect, the invention relates to liquid delivery CVD of copper electroplating base layers. The use of thermally stable copper precursors, such as (dimethyl-1,5-cyclooctadiene)Cu(I)(hfac), provides a distinct advantage for Cu CVD, especially for the deposition of the plating base layer. The enhanced thermal stability of this precursor eliminates the need for additives to stabilize the compound. Further, the thermal stability of the precursor allows liquid delivery techniques to be used to achieve reproducible film growth and uniform deposition rates. The combined liquid delivery and enhanced thermal stability allows low volatility materials to be volumetrically delivered, leading to reproducible transport and deposition. Nonetheless, an additive to further stabilize the (hfac)Cu(DMCOD) formulation can be comprised of a low cost ligand selected from the respective ligands described above in Schemes 1–3.

The utility of this approach is that it produces a conformal, thin-film with good electrical properties and high adhesion to the barrier layer (e.g., a barrier layer formed of TiN or TaN). The conformality of the deposited film can only be satisfactorily achieved through CVD techniques and the invention in such respect thereby provides a pathway to extending electroplating technologies to next-generation device geometries and dimensions. By way of specific example, a conformal plating base will be required in <0.13 μm linewidths with 4–8:1 aspect-ratio vias. The conformal deposition of these dimensions cannot be realized by presently available physical deposition methods. Thus, the CVD approach of the invention offers a viable pathway to future device generations in tandem with current low-cost electroplating processes.

The deposition of a plating base layer requires only thin conductive films (e.g., on the order of about 1000 A). The deposition process, therefore, can be relatively slow provided the electrical properties, the adhesion and the conformality are excellent. These criteria can be satisfied using a variety of (hfac)Cu(I)$L_x$ precursors, especially those stabilized with low-cost ligands depicted in Schemes 1–3. Further, CVD processes using such copper precursor yield films with good resistivities and excellent conformality. Adhesion on copper has also been determined to be excellent. By using liquid delivery of the precursors, one can produce electrically conducting plating base layers in multi-level devices.

Concerning the aforementioned problems associated with "full-fill" metallization, the liquid delivery introduction to the CVD reactor of copper precursors in accordance with the present invention, provides an enabling approach to the achievement of full-fill copper CVD. For example, the liquid delivery approach allows a copper precursor formulation to be used, wherein the copper precursor is stabilized with a low cost, coordinating additive and is at elevated temperature for only a very short period of time, thereby avoiding pre-mature thermal decomposition of the precursor. A small amount of an additive ligand can also force the chemical equilibrium of the mixture towards the starting precursor identity during vaporization and heating. Using both liquid delivery and a stabilizing additive embodies a preferred method for liquid delivery of (hfac)Cu(I)$L_x$, precursors for copper CVD.

Other embodiments of this aspect of the present invention will readily suggest themselves to those of ordinary skill in the art. For example, the addition of solutions, water, hfac hydrate or other co-reactants may be advantageously used. The copper precursors amenable to liquid delivery include Lewis base stabilized Cu(I)(hfac) species, wherein the Lewis base additive is mono-substituted, di-substituted, or unsaturated (i.e., a low-cost alkene, an alkyne, a diene), as well as other alkyl-substituted analogs of the foregoing.

The deposition of copper thin-films with useful electrical properties (low resistivity) and good adhesion to the barrier layer (TiN or TaN) are also a focus of the present invention. The desired conformality of the deposited film can only be achieved through CVD techniques. Liquid delivery CVD techniques including "flash" vaporization and copper precursor chemistry in accordance with the present invention thereby provide a pathway to "full-fill" copper metallization. Such liquid delivery technologies are enabling to next-generation device geometries and dimensions, where, for example, a conformal vertical interconnect of <0.13 micron features with 4–8:1 aspect ratio will be required. The conformal deposition of interconnects of these critical dimensions cannot be realized by currently available physical deposition methods, and the CVD methodology of the present invention in such respect offers a substantial advance in the art.

Various thermally stable, liquid and/or solid precursors other than those specifically mentioned herein may be employed to produce similar advantageous results during the CVD deposition of Cu metal for the purpose of depositing "full-fill" interconnects.

Figure 5:
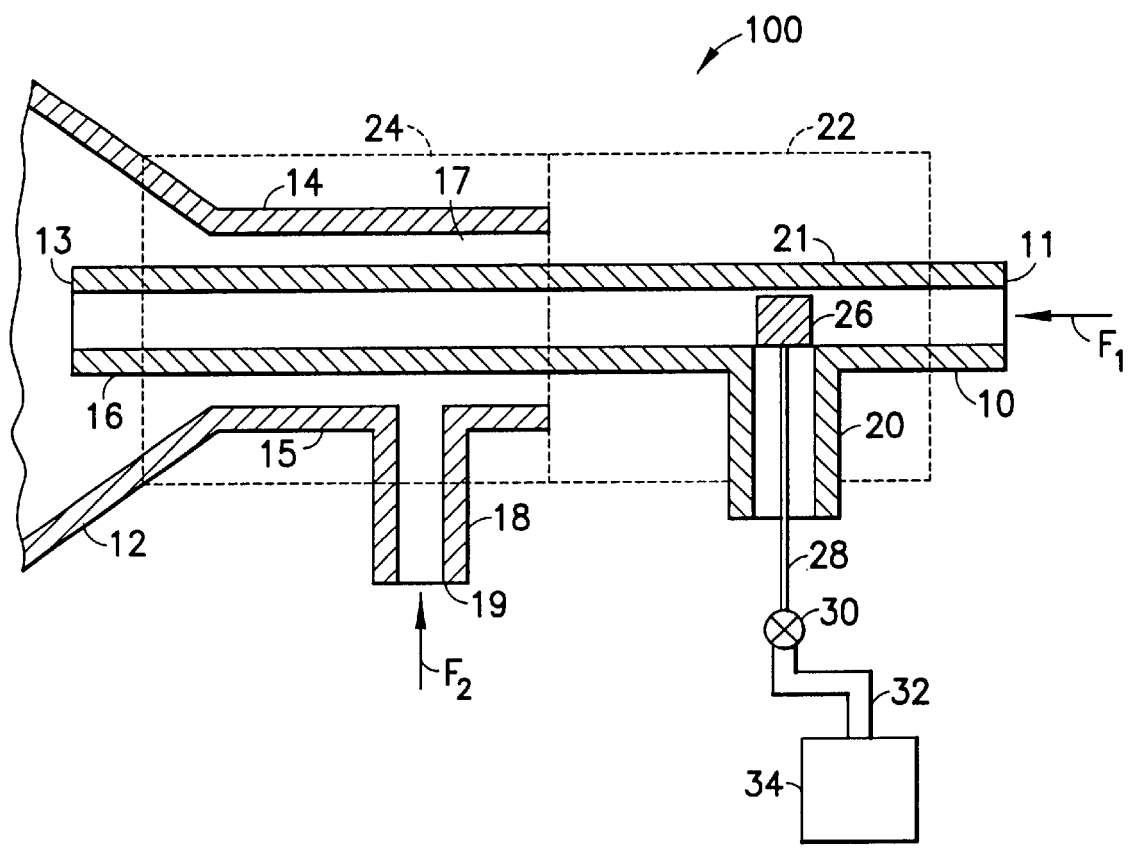
FIG. 5 is a schematic representation of a liquid delivery and vaporization system as may be used with a chemical vapor deposition (CVD) chamber for the deposition of copper-containing material on a substrate in accordance with the present invention.

FIG. 5 is a schematic representation of a liquid delivery MOCVD system 100 that may be employed in the practice of the invention for metallization in the manufacture of semiconductor devices, or otherwise for forming a copper-containing material on a substrate, using a liquid source reagent.

The delivery system 100 includes a first fluid feed passage 10 into which a first fluid is introduced in the direction indicated by arrow $F_1$. The first fluid may comprise a carrier gas, such as argon, as well as other gaseous components, e.g., source compounds, additives, co-reactants, or other species.

The first fluid feed passage 10 is connected to a gas distribution manifold at its proximal end 11, and is open at its distal end 13. The distal portion 16 of passage 10 is mounted in a housing 12 of a reactor, such as a CVD growth chamber. The distal portion 16 of the first fluid feed passage 10 thus is centrally disposed in the cylindrical portion 15 of the CVD reactor 12, to form an annular interior volume 17 therebetween.

Communicating with the annular interior volume 17 is a second fluid flow passage 18, into which second fluid is introduced in the direction indicated by arrow $F_2$, through the open end 19 of the passage. The second fluid introduced in passage 18 to the reactor may include other source reagent materials, or components or carrier gas species, such as oxygen and argon in the case of high temperature superconductor film formation systems which deposit a copper oxide superconductor material on the substrate.

Disposed in the proximal portion 21 of the first fluid flow passage 10 is a flash vaporization matrix structure 26, which is joined in liquid delivery relationship by conduit 28 and conduit 32, having check valve 30 therebetween, to liquid reservoir 34. The liquid reservoir 34 may contain one or more copper precursors in accordance with the invention. For example, the liquid reservoir 34 may be constructed and arranged to hold a solution comprising an involatile copper precursor and a suitable solvent therefor, or if the copper source reagent is a suitable liquid, then the reagent alone. The copper precursor species if of solid form at ambient conditions may be dissolved or suspended in a compatible solvent medium as more fully described in U.S. Pat. No. 5,820,664 issued Oct. 13, 1998 for "PRECURSOR COMPOSITIONS FOR CHEMICAL VAPOR DEPOSITION, AND LIGAND EXCHANGE RESISTANT METAL-ORGANIC PRECURSOR SOLUTIONS COMPRISING SAME," the disclosure of which is hereby incorporated herein in its entirety by reference.

Conduit 28 is sized and arranged (mounted on flash vaporization matrix structure 26) in such manner as to prevent premature evaporation of any volatile components (e.g., solvent constituents) of the source liquid which is flowed through conduit 28 to the vaporization matrix structure for flash vaporization thereon. The conduit 28 extends through lateral extension 20 of first fluid flow passage 10.

The delivery system 100 shown in FIG. 5 comprises a vaporization zone 22, which may be maintained at a suitable elevated temperature commensurate with the flash vaporization of reagent source liquid on the flash vaporization matrix structure 26.

Downstream from the vaporization zone 22 is an injection zone 24, wherein a second fluid is introduced via second fluid flow passage 18. The injection zone 24 is maintained at a suitable temperature, which may be somewhat less than the temperature of the vaporization zone, depending on the various constituents introduced through the respective first and second fluid flow feed passages. In some instances of the present invention, it may be advantageous to introduce a copper precursor by injection via the injection zone.

In operation, the first fluid is flowed in the direction $F_1$ through first fluid flow passage 10 into the reactor 12, being discharged at the distal open end 13 of the first fluid flow passage 10. Concurrently with such flow of gas therethrough, the reagent source liquid from reservoir 34 is flowed through conduit 32, check valve 30, and conduit 28, to the flash vaporization matrix structure 26.

The flash vaporization matrix structure 26 may be formed of any suitable material which does not deleteriously interact with the reagent source liquid or other fluid species introduced into the first fluid flow passage. The matrix structure should also be heatable to sufficient elevated temperature to effect flash vaporization of the reagent source liquid which is introduced from conduit 28 onto the surfaces of the matrix structure. The matrix structure may for example be formed of metals such as stainless steel, copper, silver, iridium, platinum, etc., as well as ceramics, high temperature glasses, quartz, chemically treated quartz, composite materials, and the like, the choice of a specific material of construction being dependent on the temperature regime which is encountered by the matrix structure, as well as the composition of the reagent source liquid and fluid flowed past the structure in the first fluid flow passage 10. Preferably, the matrix structure is constructed of an inert metal, and has a relatively high surface-to-volume ratio, as for example at least about 4, more preferably at least about 10, and most preferably at least about 100, when the surface and volume are measured in corresponding area and volume dimensional units (viz., square and cubic values of the same dimensional units).

Preferably the matrix structure is foraminous (i.e., porous or perforate) in character. The flash vaporization matrix structure may take the form of a screen, porous sintered material body, grid, or the like. The composition, surface area, and surface-to-volume characteristics of the matrix structure are selected so as to effect flash vaporization of the reagent source liquid on the surfaces of the structure, near contemporaneously with application of liquid thereon.

The conduit 28 introducing the reagent source liquid onto the matrix structure 26 may simply be an open-ended tube, i.e., a tube whose open end communicates with the matrix structure, whereby liquid issuing from the conduit flows onto the surfaces of the matrix structure for flash vaporization thereon, when the grid is heated to suitable elevated temperature. As previously discussed, conduit 28 is appropriately sized and arranged relative to the vaporization matrix structure 26 to prevent any undesirable premature evaporation of the reagent source liquid before the flash vaporization thereof on the matrix structure.

In order to enhance the dispersion and distribution of reagent solution onto the surfaces of the matrix structure, the conduit 28 may have a restriction rod (not shown) centrally disposed therein to form an interior annular conduit, whereby pressure drop in the conduit is adjusted to a desired level, and whereby liquid appropriately issues in a thin film onto the matrix structure surfaces. Alternatively, the conduit 28 may be joined to a suitable nozzle or distributor means (not shown) at the distal end of the conduit, to facilitate distribution of source reagent liquid onto the matrix structure surfaces.

The source reagent solution reservoir 34 may be associated or otherwise coupled with a suitable liquid pumping means (not shown), such as a positive displacement liquid pump which effects discharge of reagent source liquid from the reservoir through conduit 32, check valve 30, and conduit 28 to the matrix structure 26. The reagent source liquid may be introduced onto the vaporization matrix structure in a steady stream injection mode or in a pulsed injection mode from the conduit 28. In general, steady stream injection of the reagent source liquid is desirable in CVD applications since it provides the most stable concentration of the source reagent in the downstream reactor, however, pulsed injection of the reagent source liquid may be advantageous in some applications.

Preferably, the matrix structure 26 is formed of a material of construction having a high specific heat capacity, so that the structure is substantially unaffected by heat of vaporization effects, whereby the matrix structure is suitably maintained at a desirable elevated temperature for continuous operation and vaporization of the reagent source liquid. Materials of construction which may contaminate the deposited films sought to be formed from the source reagent liquid, e.g., iron, should be avoided in the practice of the invention, in applications where the composition and stoichiometry of the deposited copper-containing film are critical.

The check valve 30 between conduits 28 and 32 controls the on/off flow of reagent source liquid therethrough to the matrix structure 26 and is required to prevent the uncontrolled delivery of the source reagent solution to the matrix structure 26 under reduced pressure operating conditions.

Figure 6:
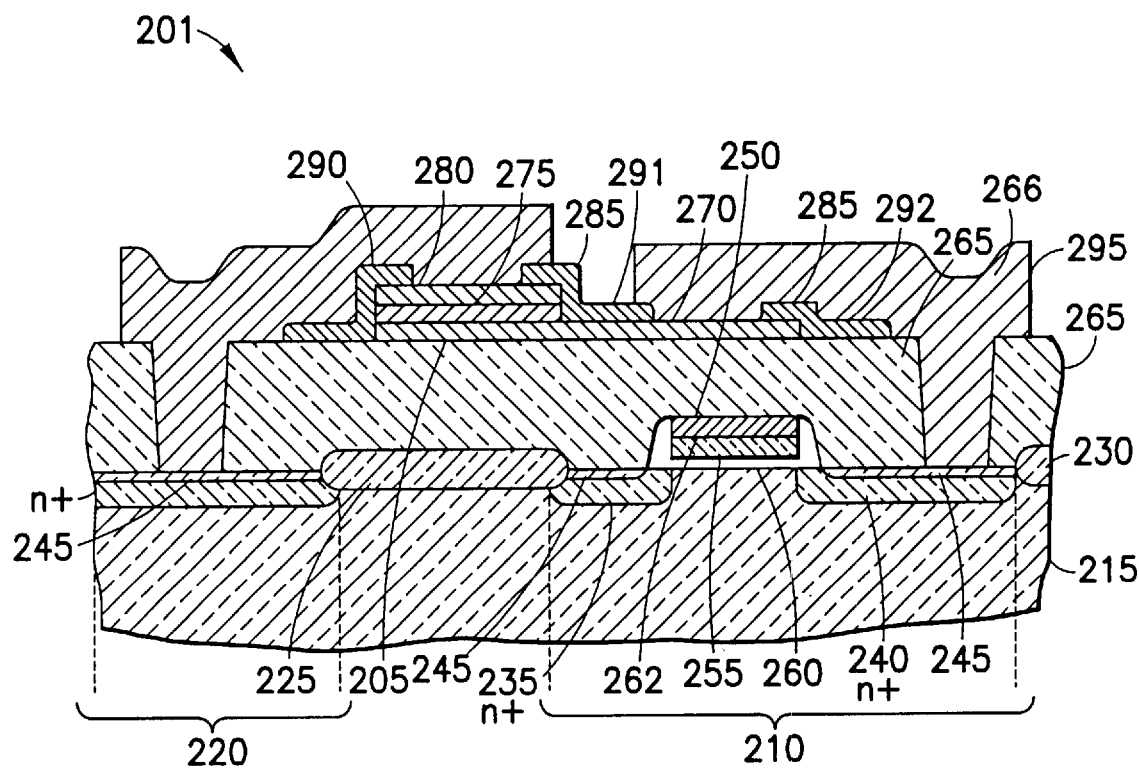
FIG. 6 schematically shows a portion of an exemplary IC with an integral capacitor that may be fabricated in accordance with the invention.

The reagent source liquid delivered to the heated matrix structure 26 is vaporized and then carried by a first fluid (carrier gas) into the deposition reaction chamber 12 for deposit of a copper-containing material on a substrate therein. The first fluid may also comprise other reagents from various upstream bubblers or other source means therefor. FIG. 6 schematically shows a portion of an exemplary IC with an integral capacitor that may be fabricated in accordance with the invention. The illustrated portion of integrated circuit 201 includes a first active device 210, such as a conventional metal-oxide-semiconductor field effect transistor (MOSFET), and a capacitor 205 employing a dielectric film layer of (Ba,Sr) titanate formed on a substrate 215, such as a silicon substrate. A drain region of a second transistor 220 is also shown. The particular types of active devices employed, e.g., NMOS, PMOS or CMOS, are based on the desired operation of the integrated circuit and are not critical for practicing the present invention. Other suitable active devices include, for example, bipolar junction transistors and GaAs MESFETs. The transistors 210 and 220 can be fabricated, for example, by conventional processing methods. In FIG. 4, the transistors 210 and 220 include field oxide regions, 225 and 230 which are formed, for example, by $SiO_2$ and operate as insulators between the transistor 210 and adjacent devices, such as the transistor 220. Source and drain regions 235 and 240 of the transistor 210 are formed by doping with n-type impurities, such as arsenic or phosphorus for NMOS. An optional layer of silicide 245 is deposited over the source and drain regions 235 and 240 to reduce the source and drain resistance, which enables greater current delivery by the transistor 210.

A gate 250 of the transistor 210 includes, for example, polysilicon 255 doped with an n-type impurity, such as by an implant or vapor doping. The gate polysilicon 255 is disposed on a $SiO_2$ spacer 260. An optional layer of silicide 262 is also deposited over the gate polysilicon 255 to reduce the electrical resistance of the gate 250. An insulating layer 265 of, for example, P-glass which is an oxide doped with phosphorus, is then deposited on the transistors 210 and 220 to provide protection to the transistors 210 and 220 and to facilitate electrical connection. Contract windows 266 are then etched in the insulating layer 265 to expose the device gate 250 and source and drain regions, such as the regions 235 and 240. Although only the drain regions of the transistors 210 and 220 are exposed in the cross-section of the integrated circuit illustrated in FIG. 4, it should be readily understood that the gate and source are exposed at other areas of the integrated circuit 1 that are outside the illustrated cross-section.

The capacitor 205 includes a first electrode 270 formed on the insulating layer surface, a dielectric thin film region 275 on the first electrode 270, and a second electrode 280 formed on the dielectric film region 275 opposite the first electrode 270. It is possible for the first electrode 270 to have a two-layer structure. Such a structure is, for example, a layer of platinum formed over a layer of Ti-nitride. Platinum alone is not a suitable electrode material, however, since it adversely chemically reacts with silicon. As a consequence, a diffusion barrier is advantageously employed as the second electrode layer which is in contact with the insulating layer surface, to substantially prevent a chemical reaction between the platinum and the silicon of the substrate 215. Suitable thicknesses for each layer of the two-layer structure are in the range of 0.01 to 0.5 μm.

It is further possible for the first electrode 270 to be a single layer structure of an appropriate conductive material. Overall suitable thicknesses for the first electrode 270, whether a one or two layer structure, are in the range of approximately 0.1 to 0.5 μm. Thicknesses less than 0.1 μm are undesirable because of its high electrical resistance while thicknesses greater than 0.5 μm are generally disadvantageous because of high fabrication cost and poor adherence. The first electrode 270 is larger than the second electrode 280 to provide electrical connection to the first electrode 270.

After formation of the capacitor 205, an insulating material 285, such as, for example, $SiO_2$ is deposited on edge regions 290, 291 and 292 of the capacitor 205 to prevent short circuits between the first and second capacitor electrodes 270 and 280 when the interconnection layer is formed. A copper interconnection layer 295 is then formed on the insulation layer and corresponding etched contact windows to electrically connect the devices 210 and 220 and the capacitor 205, by CVD using a copper precursor in accordance with the present invention. In the integrated circuit 201, the drain 240 of the transistor 210 is electrically connected to the first electrode 270 of the capacitor 280 and the capacitor's second electrode 280 is electrically connected to the source of the transistor 220.

While the invention has been described herein with reference to specific features and illustrative embodiments, it will be recognized that the utility of the invention is not thus limited, but rather extends to and encompasses other features, modifications and alternative embodiments as will readily suggest themselves to those of ordinary skill in the art based on the disclosure and illustrative teachings herein. The claims that follow are therefore to be construed and interpreted as including all such features, modifications and alternative embodiments within their spirit and scope.

What is claimed is:

1. A copper precursor composition selected from the group consisting of:

(A) [(hfac)Cu]$_2$(DMDVS).

2. A method of forming a copper-containing material on a substrate, comprising vaporizing a copper precursor composition to form a precursor vapor, and contacting said precursor vapor with a substrate to form said copper-containing material thereon, wherein said copper precursor composition includes at least one member of the group consisting of:

(A) [(hfac)Cu]$_2$(DMDVS).

* * * * *